United States Patent [19]
Eckhart et al.

[11] Patent Number: 5,848,891
[45] Date of Patent: Dec. 15, 1998

[54] APPLIANCE AND METHOD FOR ASSISTING A PATIENT IN MAINTAINING A FORWARD-MOVING FORCE ON THE PATIENT'S MANDIBULAR JAW

[75] Inventors: James E. Eckhart, Manhattan Beach, Calif.; Douglas E. Toll, Bad Soden, Germany

[73] Assignee: Ormco Corporation, Glendora, Calif.

[21] Appl. No.: 572,120

[22] Filed: Dec. 14, 1995

[51] Int. Cl.[6] .................................................. A61C 3/00
[52] U.S. Cl. .................................................................. 433/19
[58] Field of Search ................................................... 433/19

[56] References Cited

U.S. PATENT DOCUMENTS

| | | | |
|---|---|---|---|
| 4,472,138 | 9/1984 | Howe | 433/19 |
| 4,472,139 | 9/1984 | Rosenberg | 433/19 |
| 4,871,310 | 10/1989 | Vardimon | 433/19 |
| 5,324,196 | 6/1994 | Magill | 433/19 |
| 5,443,384 | 8/1995 | Franseen et al. | 433/19 |

FOREIGN PATENT DOCUMENTS

| | | | |
|---|---|---|---|
| 1680139 | 9/1991 | U.S.S.R. | 433/19 |

*Primary Examiner*—John J. Wilson
*Attorney, Agent, or Firm*—Wood, Herrron & Evans, L.L.P.

[57] ABSTRACT

The appliance includes a first member and a second member, with the second member being free of a permanent connection with the first member. The first member has an abutment/obstruction element including an abutment surface and an obstruction surface, and a mounting element for mounting the first member to a tooth on one of the maxillary or mandibular jaws. The second member has a buccally extending projection and a mounting member for mounting the second member to a tooth on the other one of the maxillary or mandibular jaws. The first and second members are mounted on the teeth so as to place the obstruction surface in generally vertical alignment with the buccally extending projection when the mandibular jaw is in its uncorrected position. This orientation causes the obstruction surface and buccally extending projection to strike one another when the patient attempts to close the mandibular and maxillary jaws with the mandibular jaw in its uncorrected position. In this manner, complete closure of the mandibular and maxillary jaws is prevented unless the mandibular jaw is advanced in a forward direction from its uncorrected position sufficient to enable the buccally extending projection to clear the obstruction surface. Once the mandibular jaw is so advanced, the patient may close the maxillary and mandibular jaws and bring the buccally extending projection into contact with the abutment surface, so as to enable the buccally extending projection and the abutment surface to assist in maintaining a forward moving force on the patient's mandibular jaw.

50 Claims, 4 Drawing Sheets

APPLIANCE AND METHOD FOR ASSISTING A PATIENT IN MAINTAINING A FORWARD-MOVING FORCE ON THE PATIENT'S MANDIBULAR JAW

This invention relates to appliances and methods for exerting or maintaining a forward-moving force on a patient's mandibular jaw and, more particularly, to an intraoral device and method for generating such an orthodontic or orthopedic force.

BACKGROUND OF THE INVENTION

Many orthodontic patients suffer from a condition known as a retrusive lower jaw, in which the lower or mandibular jaw bites in a retrusive position relative to the top or maxillary jaw. One of the problems encountered with a retrusive lower jaw is that the teeth of the lower jaw bite posterior to their normal correct biting positions against the upper teeth. Several different devices have been used by orthodontists for many years to hold the lower jaw forward from its retruded position, and after a period of time of wearing such a device, the bite becomes stable in the advanced "normal" position. This change is due to migration of the teeth within the jaws, and to differential growth and remodeling of the jaws caused by the device. In the field of orthodontics, a "normal" bite exists when the upper canine teeth bite distally relative to the lower canines, and the upper first molar mesial buccal cusp bites in the buccal groove between the lower first molar mesial and middle buccal cusps. In a frequently occurring malocclusion, the lower teeth are positioned distal or dorsal relative to that "normal" bite. This malocclusion is known generally as overbite or overjet.

One approach to the overbite/overjet malocclusion is to wear an extraoral device, known as headgear, which attaches via a face bow or j-hooks to the upper teeth via braces. The extraoral device exerts a force to the top or back of the head or the back of the neck through a tension device. This force, in turn, applies a dorsally directed force to the upper teeth and jaw. Although headgear offers one approach to correcting overbite or overjet, the device has several limitations. For example, because headgear is an extraoral device, it is highly visible and therefore has little patient appeal. Furthermore, although headgear may be permanently attached, it usually is removable, and therefore, it often is difficult to obtain patient compliance.

Overbite/overjet also may be treated using an intraoral device. Some intraoral devices work exclusively on the teeth in the upper jaw, using the palate as an anchor. These devices provide a dorsally directed force to the upper teeth and/or jaw. Specific examples include the Jones jig and the Hilgers pendulum. A further group of intraoral devices works by holding the lower jaw forward and tipping the upper jaw backward while also moving the teeth in both jaws toward a corrected position. These devices apply dorsally directed forces to the upper teeth and jaw, and ventrally directed forces to the lower teeth and jaw. Examples of such devices include Class II elastics, activators, bionators, Frankels, removable Herbsts, twin blocks and Korn appliances. Because these appliances are removable, it may be difficult to ensure patient compliance.

Overbite or overjet also may be treated with nonremovable intraoral devices which are permanently attached in the mouth. These devices work by holding the lower jaw forward and tipping the upper jaw backward, while also moving the teeth in both jaws toward a corrected bite position. Specific examples include SAIF springs, Jasper jumpers, mandibulators and Herbst appliances. One of the limitations of this group of nonremovable devices is that each of these devices creates some sort of permanent connection between the upper and lower teeth, thereby limiting the ability of a patient to open and close the jaws and mouth.

Orthotic devices also are used in the field of temporomandibular joint (TMJ) disfunction in order to advance the lower jaw for relief of pain, or to reduce clicking or locking. It is believed that such devices provide relief by decompressing the posterior ligaments of the condyle disk, by reducing the ability to clench the jaw-closing muscles when the lower jaw is forward, and by "recapturing" the displaced condyle disk onto the head of the condyle of the lower jaw. Devices currently being used to treat TMJ include a plastic orthotic portion or portions attached to the teeth and jaw with plastic indices attached to the opposing teeth so as to hold the lower jaw open and forward. However, such devices have several limitations because they are relatively bulky and do not allow the teeth in both jaws to be moved orthodontically while holding the jaw forward.

Orthodontic or orthopedic devices also are used in the field of sleep disorders to treat snoring or obstructive sleep apnea. In the sleep disorder arena, it is known that snoring and obstructive sleep apnea usually are due, at least in part, to the tongue falling dorsally during sleep, thereby pressing on the soft palate and reducing or blocking the airway. Traditional antisnoring dental devices employ the principle of holding the lower jaw forward, thereby keeping the tongue out of the throat during sleep. Examples include bionators, activators, Herbsts and Jasper jumpers as mentioned above, as well as other devices such as the Snoreguard, SNOAR, NAPA, ASD and Feldman/Shapiro appliances. Although these devices usually offer some relief in the treatment of snoring or obstructive sleep apnea, they have several limitations. For the devices which are removable, patient compliance may be a problem. In addition, several of the appliances are quite bulky. Furthermore, many of the appliances result in morning jaw stiffness. Finally, the devices are difficult to wear if the teeth are being moved orthodontically.

Therefore, it would be extremely advantageous to have an appliance and method of treatment of overbites, of TMJ problems, and of snoring and sleep apnea, which may not be removed by the patient and which is aesthetically pleasing. It also would be beneficial to have such a device and method which do not permanently connect the jaws, thereby allowing the patient greater jaw movement and comfort while still providing a nonremovable device so that compliance is not a problem. In addition, it would be desirable for such a device and method to enable the teeth in both jaws to be moved orthodontically while holding the jaw forward, as well as to avoid the morning jaw stiffness present with many of the removable appliances. Furthermore, it would be beneficial to have such a device which is less bulky than traditional devices, thereby enhancing patient appeal.

SUMMARY OF THE INVENTION

This invention is directed to an appliance and method for assisting a patient in maintaining a forward-moving force on the patient's mandibular jaw. The appliance includes a first member and a second member. The first member has an abutment/obstruction element and a mounting element for mounting the first member to a tooth on one of the maxillary or mandibular jaws. The abutment/obstruction element further includes an abutment surface and an obstruction surface. The second member has a buccally extending projection and a mounting member for mounting the second member to a tooth on the other one of the maxillary or mandibular jaws, with the second member being free of a permanent connection with the first member.

The first and second members are mounted on the teeth so as to place the obstruction surface in generally vertical alignment with the buccally extending projection when the mandibular jaw is in its uncorrected position. This orientation causes the obstruction surface and buccally extending projection to strike one another when the patient attempts to close the mandibular and maxillary jaws with the mandibular jaw in its uncorrected position. In this manner, complete closure of the mandibular and maxillary jaws is prevented unless the mandible is advanced in a forward direction from its uncorrected position sufficient to enable the buccally extending projection to clear the obstruction surface. Once the mandibular jaw is so advanced, the patient may close the maxillary and mandibular jaws and bring the buccally extending projection into contact with the abutment surface, so as to enable the buccally extending projection and the abutment surface to assist in maintaining a forward moving force on the patient's mandibular jaw.

This invention offers several benefits and advantages over traditional devices and methods. Because the inventive appliance does not connect the jaws, a patient is able to enjoy greater jaw movement and comfort while receiving the necessary treatment. In addition, the appliance enables the teeth in both jaws to be moved orthodontically at the same time the lower jaw is being moved forward by the forces exerted by the inventive appliance. Furthermore, the appliance is relatively compact, invisible to the casual observer and in most embodiments, nonremovable by the patient, thereby enhancing patient appeal and patient compliance. Also, the appliance usually does not cause morning jaw stiffness found in many of the traditional devices.

These and other benefits and advantages will become readily apparent to those of ordinary skill in the art upon review of the following brief description of the drawings and detailed description of the invention.

DETAILED DESCRIPTION OF THE INVENTION

Figure 1:
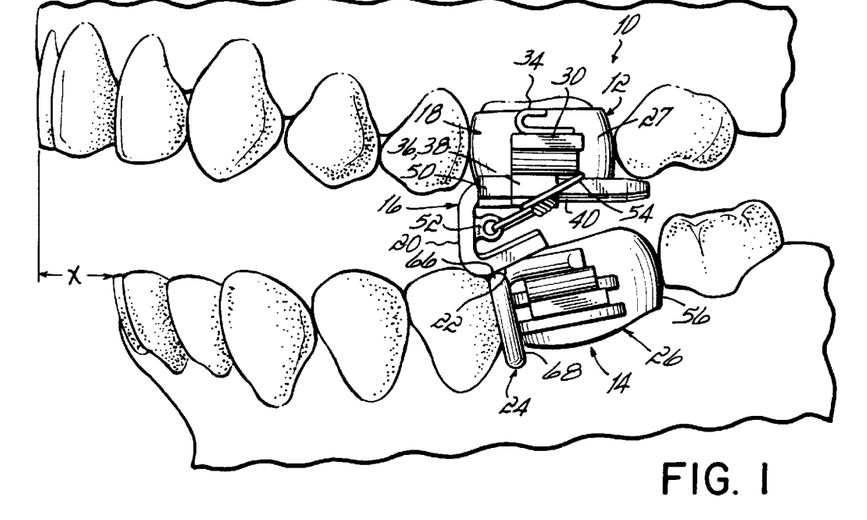
FIG. 1 is a view of the left side of the maxillary and mandibular jaws of a patient having a retrusive lower jaw, with the retrusive lower jaw in its uncorrected position and the maxillary and mandibular jaws in an open relationship.

Referring to FIG. 1, the appliance 10 is shown mounted to the first molars on the left side of a patient having overbite or overjet, in which the lower jaw is in a retrusive position (as shown by the distance X). The appliance includes a first member 12 mounted on the first molar of the maxillary jaw and a second member 14 mounted on the first molar of the mandibular jaw. The first member 12 includes an abutment/obstruction element 16 and a mounting element 18 for mounting the first member 12 to the tooth, with the abutment/obstruction element 16 having an abutment surface 20 and an obstruction surface 22. The second member includes a buccally extending projection 24 and a mounting member 26 for mounting the second member 14 to the first molar on the mandibular jaw.

Figure 2:
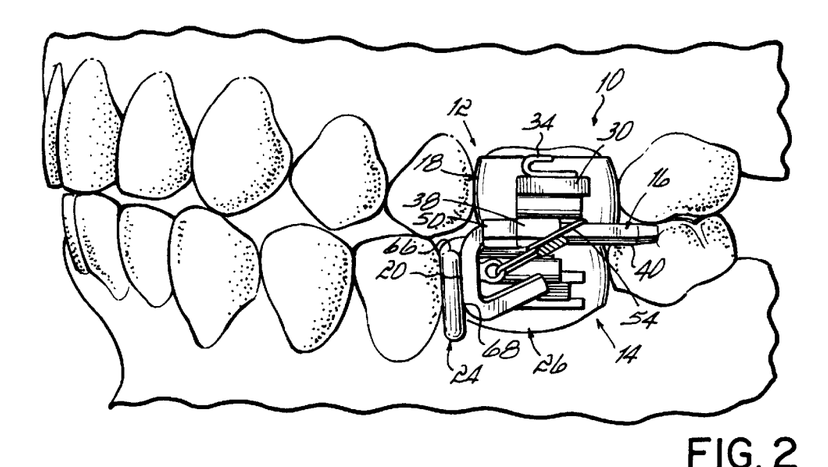
FIG. 2 is a view of the left side of the maxillary and mandibular jaws of a patient having a retrusive lower jaw, with the lower jaw in a corrected position and the maxillary and mandibular jaws in a closed bite relationship.
Figure 5A:
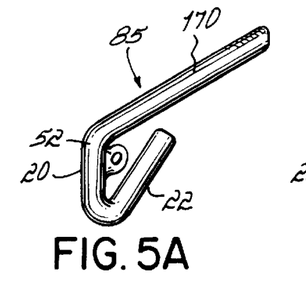
FIG. 5A is a perspective view of an embodiment of the abutment/obstruction element of the invention.
Figure 5B:
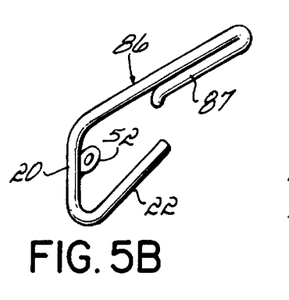
FIG. 5B is a perspective view of a further embodiment of the abutment/obstruction element.
Figure 5C:
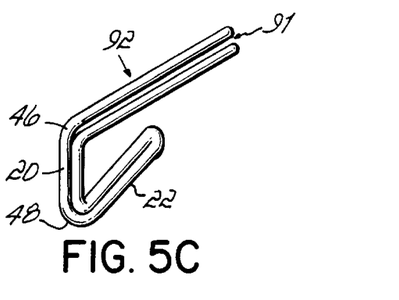
FIG. 5C is a perspective view of yet another embodiment of the abutment/obstruction element.
Figure 5D:
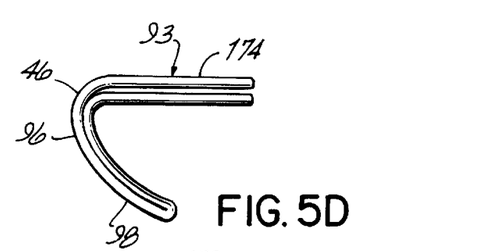
FIG. 5D is a side view of another embodiment of the abutment/obstruction element.

As seen in FIG. 1, the first and second members 12, 14 are mounted so as to place the obstruction surface 22 in generally vertical alignment with the buccally extending projection 24 when the mandibular jaw is in its uncorrected position. This alignment causes the obstruction surface 22 and buccally extending projection 24 to strike one another when the patient attempts to close the mandibular and maxillary jaws with the mandibular jaw in its uncorrected position, thereby preventing complete closure of the mandibular and maxillary jaws. However, once the mandibular jaw is advanced in a forward direction from its uncorrected position sufficient to enable the buccally extending projection 24 to clear the obstruction surface 22, the patient may close the maxillary and mandibular jaws and bring the buccally extending projection 24 into contact with the abutment surface 20 as shown in FIG. 2. This contact between the buccally extending projection 24 and the abutment surface 20 enables the projection 24 and abutment surface 20 to assist in maintaining a forward moving force on the patient's mandibular jaw. In this particular embodiment of the appliance 10, the initial forward movement of the mandibular jaw required for the buccally extending projection 24 to clear the obstruction surface 22, is generated by the patient. However, in other embodiments of the appliance such as shown in FIG. 5D, the first and second members may be designed in such a way that they assist the patient in the initial advancement of the mandibular jaw in a forward direction as the patient closes the maxillary and mandibular jaws.

Usually, the appliance 10 is mounted on the first molars of the maxillary and mandibular jaws, although depending upon the particular patient and condition being treated, other teeth may be used instead. In addition, the appliance 10 generally is used in combination with another matching appliance positioned on the opposite side of a patient's jaws. For example, referring to FIGS. 1 and 2, in addition to the appliance 10 shown mounted on the left side of the patient's mouth, the patient might have a matching mirror-image appliance mounted on the first molars positioned on the right side of that patient's mouth. However, depending upon the particular treatment needs of a patient, the appliance may be used on a single side of a patient's mouth without a matching appliance positioned on the opposite side of the mouth.

Figure 3:
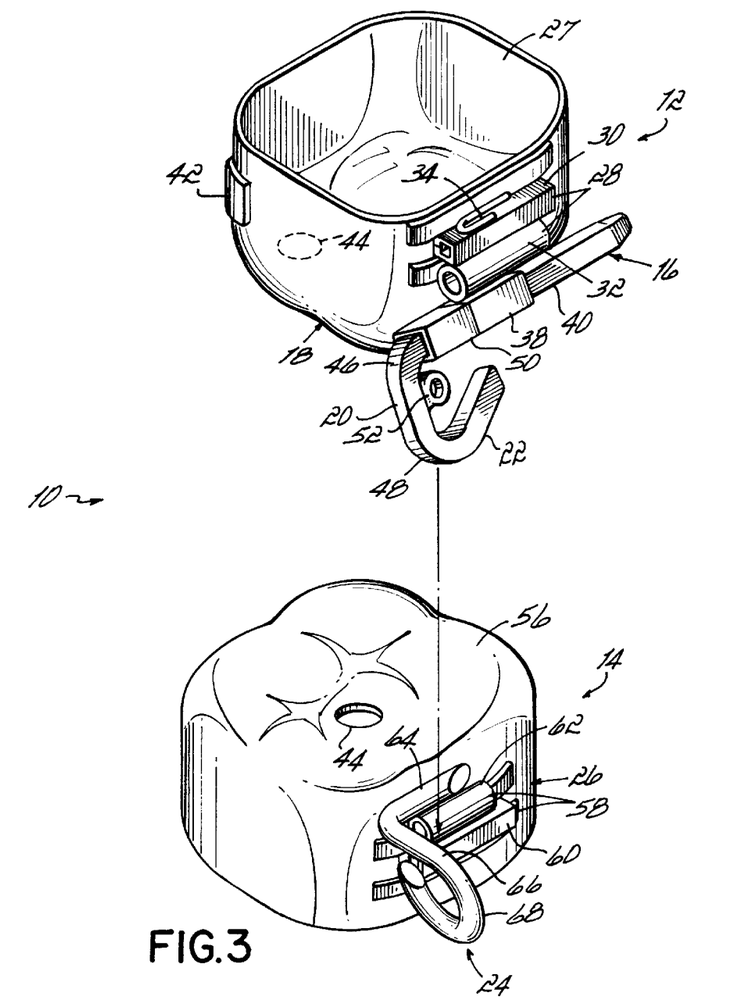
FIG. 3 is a perspective view of the first and second members of an embodiment of the invention.
Figure 4:
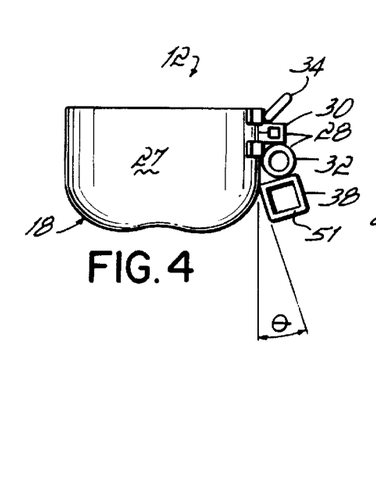
FIG. 4 is a mesial or front view of the embodiment of the mounting element of the first member shown in FIG. 3.

Referring to FIGS. 3, 4 and 7, the first and second members 12, 14 of this embodiment of the appliance 10 will be discussed in more detail. Referring to FIGS. 3 and 4, the mounting element 18 of the first member 12 includes a stainless steel veneer crown 27 having several attachments. One of the attachments is a combination tube 28 mounted to the buccal surface of the stainless steel crown 27. The tube 28 has an archwire tube 30, an auxiliary tube 32 and a hook 34. Also mounted to the stainless steel crown 27 is a complementary mounting section 36, which in this embodiment is a square tube 38 for slidably receiving a mounting section 40 of the abutment/obstruction element 16. The mounting section 40 includes a stem which is slidingly engageable with the square tube 38 of the mounting element 18. As used herein, the term "stem" means a connecting or supporting part of the abutment/obstruction element, sized to engage the mounting element of the appliance. The crown 27 further includes a purchase ledge 42 along the mesial-lingual surface of the crown and a vent hole 44 in the buccal slope of the mesial-lingual cusp, for removal of the crown 27 after treatment using a Chastant stainless steel crown removing plier or other modified band remover.

Referring to FIG. 3, the abutment/obstruction element 16 includes an abutment surface 20 extending in a generally gingival-occlusal direction between a gingival extremity 46 and an occlusal extremity 48 and an obstruction surface 22 extending generally distally and gingivally upward from the occlusal extremity 48 of the abutment surface 20, at an angle of from about 45° to about 65° relative to the longitudinal axis of the abutment surface 20. The abutment/obstruction element 16 includes the mounting section 40 extending distally from the gingival extremity 46 of the abutment surface 20 substantially parallel to the occlusal plane, at an angle of about 90° relative to the longitudinal axis of the abutment surface 20.

Referring to FIGS. 1, 2 and 3, the mounting section 40 of the abutment/obstruction element 16 is slidingly engaged by the complementary mounting section 36 on the crown 27, which in this embodiment, is the square tube 38. The mounting section 40 includes a surface feature, such as a slide-on collar or shim 50, positioned on the mounting section 40 at the mesial opening of the square tube 38, which contacts the lip or rim 51 (FIG. 4) of the mesial opening of the square tube 38, thereby maintaining the positioning of the abutment/obstruction element 16 relative to the stainless steel crown 27 as a distally directed force is exerted on the element 16 from the buccally extending projection 24 when the patient's jaws are in a closed bite position. If desired, a "dog leg" bend, welded stop, nick or the like may be used in place of the slide-on shim as the surface feature. The abutment/obstruction element 16 further includes a metal loop 52, such as a section of tubing or wire formed into a loop, positioned on the distal side of the abutment surface 20. As shown best in FIGS. 1 and 2, this loop 52 is used in combination with a ligature wire 54 which passes through the loop 52 and wraps around the square tube 38 and mounting section 40, to assist in holding the abutment/obstruction element 16 in position when the patient's jaws are in an open relationship.

Referring to FIGS. 3 and 7, the second member 14 of this particular embodiment of the appliance 10 will be discussed in more detail. The mounting member 26 includes a stainless steel crown 56 having a combination tube 58 mounted on its buccal surface. As best seen in FIG. 7A, the combination tube 58 includes an archwire tube 60 and an auxiliary tube 62. The buccally extending projection 24 of the second member 14 includes a mounting section 64 which is attached to the buccal surface of the crown 56 in an occlusal and parallel relationship relative to the combination tube 58 (see FIG. 3). The buccally extending projection 24 further includes an obstruction surface 66 (see FIG. 3) which contacts the obstruction surface 22 of the abutment/obstruction element 16, and an abutment surface 68 (see FIG. 2) which contacts the abutment surface 20 of the abutment/obstruction element 16. As seen most clearly in FIG. 7A, the buccally extending projection 24 is formed as a loop. This loop design provides a smooth, rounded surface for contact with the cheek and also provides a strong abutment surface 68 (FIG. 2) for contact with the abutment surface 20 of the abutment/obstruction element 16.

Referring to FIGS. 3 and 4, the square tube 38 of the first member 12 preferably is torqued at an angle $\theta$ of about 20° relative to the plane of the buccal surface of the crown 27. This offset enables the abutment and obstruction surfaces 20, 22 of the abutment/obstruction element 16 to clear the combination tube 58 on the second member 14 when the patient advances the lower jaw and closes the bite.

The first and second members 12, 14 of this embodiment of the appliance may be made by starting with stainless steel crowns, such as crowns made of 303 half-hard stainless steel, for example. If desired, the crowns may be made of a 300 Series stainless steel, for example, 304 half-hard stainless steel. If a harder metal is desired, 17-7 PH stainless steel may be appropriate. In order to accommodate variation in tooth size among patients, it is advantageous to have crowns of varying sizes, for example, sizes 1 through 7. Such crowns are available from Ormco Corporation of Glendora, Calif. In preparing the first and second members, the combination tubes are welded to the stainless steel crowns, with the mesial end of the combination tube aligned with the center of the mesial buccal cusp of the crown. The combination tubes used should have a relatively low profile, since the abutment/obstruction element will bite buccally relative to the combination tube of the second member. Suitable combination tubes having zero distal offset are available from Ormco Corporation of Glendora, Calif. These combination tubes are available with and without a hook, include a distal extension and come in right side and left side models. In addition, these combination tubes are available in two different sizes. In one size, the archwire tube is 0.018"×0.025" with a 0.045" or 0.051" auxiliary tube, while the other size has a 0.022"×0.028" archwire tube with a 0.045" or 0.051" auxiliary tube. These particular Ormco combination tubes are available under part numbers 534-1845, 534-2245, 524-1845, 524-2245, 536-1845, 536-2245, 526-1845 and 526-2245.

It is preferred to use combination tubes in forming the first and second members of the appliance for several reasons. For example, because the abutment/obstruction element or buccally extending projection may obstruct one's view in attempting to guide an archwire into the archwire tube, the archwire tube has a larger, more visible orifice, thereby facilitating insertion of the archwire into the tube. Also, a lip bumper may be used with the auxiliary tube to increase arch length and prevent lower molar rotation from the force exerted by the abutment/obstruction element of the opposing member, without having to tie up the arch with braces, thereby allowing the buccal teeth to erupt and the posterior open bite (created by the mandibular advancement) to close. In addition, if the anterior teeth are already straight, hygiene is easier if a lip bumper is used instead of braces on the anteriors.

Also, a lower lingual arch may be used with a lingual sheath on the lingual surface of the mounting member to increase arch length and prevent lower molar rotation from the force exerted by the abutment/obstruction element of the opposing member, without having to tie up the arch with braces.

The combination tube is oriented on the stainless steel crown so that the auxiliary tube is oriented occlusally and the archwire tube is oriented gingivally. This orientation provides a better ledge for soldering and provides a lower profile for the abutment/obstruction element of the opposing member to bite over, given the slight lingual inclination of the buccal surface. In addition, in welding the combination tube to the crown, the combination tube should be positioned sufficiently gingivally in order to provide room for the square tube (in the case of the first member) or the buccally extending projection (in the case of the second member), which will be soldered occlusally above the welded combination tube.

In order to increase retention of the crown on the tooth, the interior surface of the crown preferably is sand blasted. If desired, this sand blasting may be done using a microetcher as is available from Danville Engineering of Danville, Calif. As an alternative to the sand blasting, wire mesh may be welded on the inside of the crown. For example, a 3 mm ×3 mm piece of wire mesh may be welded inside the buccal surface of a crown used on a mandibular tooth or inside the lingual surface of a crown used on a maxillary tooth. Such wire mesh is available from O.I.S./Stratford Cookson of Rockville Centre, N.Y., under the product number 031-6000.

For crowns to be used on maxillary teeth, a wire horizontal ledge similar to a cleat is welded onto the axial surface at the mesial lingual corner of each of these crowns. The gingival-occlusal location of the ledge may be varied. This ledge serves as a "purchase" ledge for a Chastant crown removing plier when the crown is removed following treatment. A 3 mm long section of 0.021"×0.028" stainless steel wire is suitably used for forming the ledge, and the wire is welded flat onto the crown. The purchase ledge is recommended for crowns used on maxillary teeth because crowns on such teeth generally are removed from the lingual side given the slanting of that particular axial surface. However, for crowns to be used on the mandibular teeth, it usually is unnecessary to provide this purchase ledge. Because a crown positioned on a mandibular tooth typically is removed from the buccal side of the tooth, the combination tube attached to the crown usually provides adequate purchase.

A vent hole is cut in the occlusal surface of each crown in order to enable a doctor to remove the crown using a Chastant stainless steel crown removing plier. The vent hole suitably is approximately 2 mm in diameter to accommodate the post of the Chastant crown removing plier, and is placed in the buccal slope of the mesial lingual cusp of a crown to be used on an upper molar, and in the lingual slope of the mesial buccal cusp of a crown to be used on a lower molar.

The buccally extending projection is prepared by bending a 0.059" or 0.065" diameter wire. A 300 Series stainless steel wire may be used to advantage, including 304 half-hard, for example. Alternatively, if a harder metal is desired, a metal such as 17-7 PH stainless steel may be used. One end of the wire is wrapped around a mandrel in order to form a loop having an inside diameter of about 0.059" and an outside diameter of about 0.177". A bend having an angle of from about 80° to about 90° is placed in the wire approximately 0.296" away from the most buccally extended portion of the loop, and the trailing or mounting section is trimmed to have a length of about 0.256". In addition, a chamfer is formed on the buccal surface of the distal end of this mounting section by grinding the distal end at an angle, in order to give the mounting section a relatively low profile. The mounting section of the buccally extending projection then may be soldered onto the crown using a silver solder or the like. If desired, flux may be placed in the loop and at the approximately 80° to 90° bend. Then, the solder should be heated into both spots. The solder at the approximately 80° to 90° bend then is refluxed, and the piece is set aside for the moment, to be subsequently soldered to the stainless steel crown. At this point, antiflux, e.g., milk of magnesia or antiflux available from Link Industries of Cannon Beach, Oreg., may be placed into the lumens of the combination tube on the stainless steel crown in order to prevent solder from clogging the tubes. Flux also may be placed on the stainless steel crown occlusal to the combination tube, and solder may be heated onto the stainless steel crown. If desired, a blazer torch which uses butane fuel may be used. At this point, the tube lumens may be antifluxed again and the solder may be refluxed. At this point, the 0.059 inch or 0.065 inch wire may be soldered in place. The mounting section should be aligned parallel to the occlusal plane but submerged slightly below it. In addition, the mounting section should be positioned on the crown so that the mesial surface of the loop of the buccally extending projection is flush with the plane formed by the mesial surface of the stainless steel crown. With the wire soldered in place, the soldered wire may be quenched. Also, the projection/crown combination may be ultrasonically cleaned in tartar and stain removing solution. In its finished form, the buccally extending projection extends outwardly from the crown at an angle of from about 80° to about 90° and has a buccally extending length of about 0.296" from the buccal surface of the crown to the most buccally extending portion of the projection.

In completing the formation of the mounting element of the first member, a square tube is soldered to the buccal surface of the stainless steel crown. The square tube is preferably made of stainless steel, such as a 300 Series stainless steel (for example, 304 half-hard) or a 17-7 PH stainless steel, and has an inner diameter of 0.063"×0.063" with a wall thickness of about 0.0175". In addition, a suitable square tube has a length of from about 0.120" to about 0.160". Such square tubes are available from Ormco Corporation of Glendora, Calif., under the part number 070-2250. In soldering the square tube, a 3" piece of 0.060" square wire is dipped into antiflux and then inserted through the square tube as a means of holding the square tube. Then, antiflux is placed around the mesial and distal rim interfaces between the square tube and the holding wire. Two contiguous sides of the square tube then are fluxed and solder is heated onto these two contiguous sides. The two sides are then refluxed. In order to prevent solder from clogging the auxiliary and archwire tubes, antiflux may be placed into the lumens of the combination tube on the stainless steel crown. Then flux is placed on the crown occlusal to the combination tube, followed by heating solder onto the crown. The lumen of the combination tubes then are antifluxed again, and the solder is refluxed. Then, the square tube 38 may be soldered to the stainless steel crown 27. The square tube 38 should be placed so that the mesial opening of the square tube is flush with the mesial openings of the combination tube 28, and torqued so that the square tube 38 is at an angle ⊖ of about 20° relative to the plane of the buccal surface of the crown, with one side of the square tube resting against the auxiliary tube 32 of the combination tube, as shown best in FIG. 4. In order to enhance the strength of this solder joint, the solder joint should completely wrap two sides of the square tube. The square tube may be microetched by sandblasting prior to soldering, to increase the retentiveness of the solder. Once the square tube 30 has been soldered onto the crown 27, an undercut may be formed in the solder joint along the distal lingual portion of the square tube 38. This undercut may be formed with a Joe Dandy disc or the like, and provides an indent for the tie back ligature used to secure the abutment/obstruction element to the stainless steel crown 27.

The abutment/obstruction element 16 may be made by forming a section of 0.060" square wire, for example, 303 half-hard stainless steel wire. Such wire is available from Ormco Corporation of Glendora, Calif. The wire may be formed by bending with a 3-prong Masel 816 bar bending plier or another sturdy 3-prong plier. In order to accommodate the 0.060 square inch wire, the groove of the Masel 816 plier may be enlarged using a Joe Dandy disk or other grinding device. The three sections of the abutment/obstruction element 16 are created by forming two bends in the wire. Using the Masel bar bending plier or other sturdy 3-prong plier, a first bend is formed in the wire which creates the obstruction surface portion 22 of the abutment/obstruction element 16. This obstruction surface portion 22 is bent back and up at an angle of from about 45° to about 65° relative to the longitudinal axis of the abutment surface 20. The second bend establishes the length of the abutment surface 20 and is formed so as to create an angle of about 90° between the longitudinal axis of the abutment surface 20 and the longitudinal axis of the mounting section 40. Typically, when the abutment/obstruction element 16 is formed, all three sections are formed in a single plane, although this is not required. The free or trailing end of the mounting section 36 then may be tapered and smoothed using a lathe grinding wheel or the like. Suitable embodiments of the abutment/obstruction element 16 may be formed having an obstruction surface length from about 0.29" to about 0.46", and an abutment surface length from about 0.27" to about 0.40". Such abutment/obstruction elements are available from Ormco Corporation of Glendora, Calif., under the part numbers 070-2253 and 070-2254.

In completing the formation of the abutment/obstruction element 16, the metal loop 52 is soldered onto the opposite side of the abutment surface, approximately midway between the gingival and occlusal extremities of the abutment surface. Flux may be placed onto the opposite side, followed by heated solder and refluxing. Then, the loop may be soldered in place. Care should be taken in positioning the loop 52 on the abutment/obstruction element 16, because if the loop 52 is soldered too near to the mounting section 40, the abutment/obstruction element 16 will not be able to slide all the way into the square tube 38. In addition, the solder should be applied carefully so as not to get solder into the approximately 45°–65° bend and the approximately 90° bend in the abutment/obstruction element 16. By confining the solder to the area where the loop 52 is applied, a doctor may still alter the approximate 90° angle and the approximately 45°–65° angle of the element as needed in treating a particular patient. Suitable metal loops are available from Ormco under Part Nos. 622-0151 and 622-0145.

When installing and using the appliance, the doctor should separate the teeth, although no tooth reduction is necessary. When installing the particular embodiment of the invention shown in FIG. 1, a stainless steel crown 27 having a combination tube 28 and square tube 38 is fitted onto each first molar of the maxillary jaw. In addition, a crown 56 having a combination tube 58 and buccally extending projection 24 is mounted to each first molar on the mandibular jaw. The crown 27, 56 sizes selected should fit properly on the teeth. If any one of the crowns 27, 56 is too big, it may fall off easily, while if it is too small, the patient may not be able to bite down completely. The crowns 27, 56 should be seated enough so that they do not jack the bite into an open position. If any crown 27, 56 is left high, it will intrude the particular molar over time, making banding of the molar difficult later on. Because length of crown is very important for retention, the crown length should be trimmed only the minimum amount necessary to allow proper seating of the crown without injuring the gum. In determining whether the crown 27, 52 is seated properly, it is helpful to look through the vent hole 44 and to look at the approximation to the tooth's occlusal surface. If desired, the stainless steel crowns may be tightened by circumferentially crimping the crowns in the gingival margins with a Tweed arch bending plier or the like. As another option, a shim or shims of band material may be welded on the inside of the crown in order to obtain a tighter fit.

Before cementing the crowns, the patient's bite should be checked with all four crowns in place. The bite should be checked with the patient biting in an overcorrected or slightly Class III incisor relationship, with the upper and lower midlines lined up over one another. The alignment of each first member relative to its corresponding second member should be checked by verifying that the distance from the mesial opening of the square tube to the buccally extending projection is roughly equal on right and left sides of the mouth, and that this distance is short enough so that the abutment/obstruction element 16 is capable of forming the necessary relationship with the buccally extending projection 24. If need be, these distances may be varied slightly by rotating particular crowns on the teeth.

If the crowns fit stably without cement, the abutment/obstruction elements 16 should be roughly fitted prior to the cementation. In deciding whether to use abutment/obstruction elements 16 having a relatively shorter or relatively longer abutment surface 20, the doctor should look at the molars in the super-class I position. If the molars are apart, then long vertical legs may be necessary. If, however, there is very little cheek space, then short vertical legs may be required. In order to get the abutment/obstruction element 16 to remain advanced a particular distance within the square tube 38, mounting section 40 of the element 16 may have placed upon it a spacer or collar, for example, a section of square tubing similar to the square tube used to hold the abutment/obstruction element 16. This spacer 50 is placed on the mounting section of the abutment/obstruction element 16 prior to inserting the mounting section into the square tube 38 which is soldered onto the crown 27.

Figure 6:
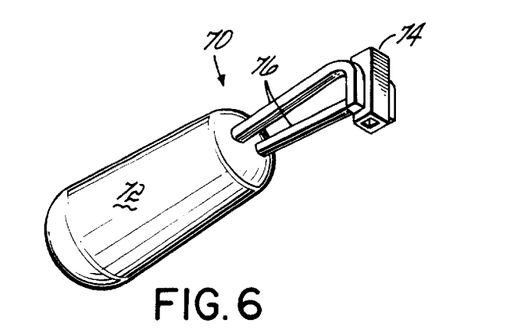
FIG. 6 is a perspective view of a wire holding tool for use in adjusting the abutment/obstruction element.

Alternatively, a nick may be placed along the mounting section of the abutment/obstruction element by "dinging" two corners of the mounting section using a heavy wire cutter or the like. Alternatively, a raised "stop" may be placed on the mounting section by welding a piece of metal to a portion of the mounting section 40. Alternatively, a dog leg bend may be placed in the mounting section using a sturdy 3-prong plier. These various mechanisms all serve the same general purpose of preventing the abutment/obstruction element from being moved further into the square tube. If desired, some buccal or lingual flare or torque may be added to the abutment/obstruction element so that the element fits properly relative to the combination tube of the second member. This flaring or torquing may be accomplished by holding the mounting section of the abutment/obstruction element with the square wire holding tool and bending the abutment surface buccally or lingually with a plier. This wire bending tool 70 includes a handle 72 for grasping the tool as well as a section of 0.063" square tube 74 soldered to a pair of heavy gauge connector bars 76 which are mounted in the handle of the bar bending tool.

The positioning and length of the trailing or free end of the abutment/obstruction element's obstruction surface 22 and mounting section 40 should be checked to see that they do not hurt the cheek. The free end of the obstruction surface 22 may have to be bent buccally, lingually and/or gingivally to avoid the gingival mucosa and the cheek.

If the abutment/obstruction elements 16 selected are comfortable, and the doctor believes that the crowns will fit properly in their same positions when cemented, it is easiest to tie the abutment/obstruction element 16 into the upper crowns while the crowns are out of the patient's mouth, and then to cement the crowns in place. If there is uncertainty as to the comfort of the abutment/obstruction elements 16 or the positioning of the crowns, the crowns may be cemented without the abutment/obstruction elements 16 in place. If the doctor chooses to cement the crowns in place without the abutment/obstruction elements attached, once the cement has set for about fifteen minutes, the abutment/obstruction elements may be tied in place. When inserting the abutment/obstruction elements, it is easiest to place a steel ligature wire through each abutment/obstruction element loop before inserting the element into the square tube 38. Then, after inserting the abutment/obstruction element into the square tube, one end of the ligature wire is passed around the distal extension of the mounting section of the abutment/obstruction element and then twisted into a tie. Once the ligature wire 54 ends are tied and cut, the ligature pigtail may be tucked between the obstruction element and the abutment/obstruction mounting element, as shown in FIGS. 1 and 2. The crowns may be cemented with a cement such as Ormco Corporation's Protech® glass ionomer cement or the like, using about six drops of liquid per crown. Most of the excess cement goes out the vents and is easily removed. However, some of this excess cement should be left over the vent orifice in anticipation of washout. If washout subsequently occurs, the vent hole may be filled with acrylic at that time.

The doctor should instruct the patient that, with this particular embodiment of the appliance, the abutment/obstruction element 16 and buccally extending projection 24 are present to guide the bite and to assist in maintaining a forward moving force on the patient's lower jaw once the patient has moved the lower jaw forward enough so that the buccally extending projection may clear the obstruction surface, and that the abutment/obstruction element 16 and buccally extending projection 24 are not present in the mouth for the patient to chew against these elements. Most patients will be able to eat much better after a week or so of having an appliance 10 or pair of appliances in the mouth, and the patient should be instructed to call the doctor if the abutment/obstruction elements 16 seem too long.

If the appliance 10 is being used to perform a Class II correction, depending upon the particular patient, the correction usually may be done in one move using the appliance or pair of appliances in the mouth. In most cases, it will be advantageous to position the abutment/obstruction element 16 in the square tube 38 so that there is actually an overcorrection of about 2 mm to 3 mm when the patient's jaws are in a closed position and the abutment surface 20 of the abutment/obstruction element 16 is resting against the abutment surface 68 of the buccally extending projection as shown generally in FIG. 2.

In using the appliance 10, the appliance should not be placed on the deciduous second molars unless the doctor is not concerned that the tooth may be lost relatively early. In addition, if using the deciduous second molars, the doctor should check to be sure that these teeth have sufficient root before the appliance 10 is placed on these teeth. In addition, maxillary width insufficiency should be corrected before placing the appliance on a patient's teeth, because the abutment/obstruction element 16 usually will be unable to bite buccally of the lower molars unless the upper molars are wide enough. Also, upper crowding and insufficient incisor torque should be corrected prior to placing the appliance on a patient's teeth, so that the incisors will not interfere with advancing the mandible enough to correct the Class II malocclusion. For younger patients, if the appliance is placed on the first permanent molars, the doctor should evaluate the cheek space near the distal side of the first molars carefully to be sure that the patient has sufficient room for the abutment/obstruction elements 16 without cheek biting. In addition, it may be appropriate to shorten the mounting section of the abutment/obstruction element 16 by cutting off a portion of the trailing or free end when the appliance is used with younger patients. Also, because the lower first molars may rotate mesially under pressure from the abutment/obstruction elements 16 on the buccally extending projections, it is best to prevent their rotation by using a lower archwire or a lip bumper or a lingual arch.

Figure 2A:
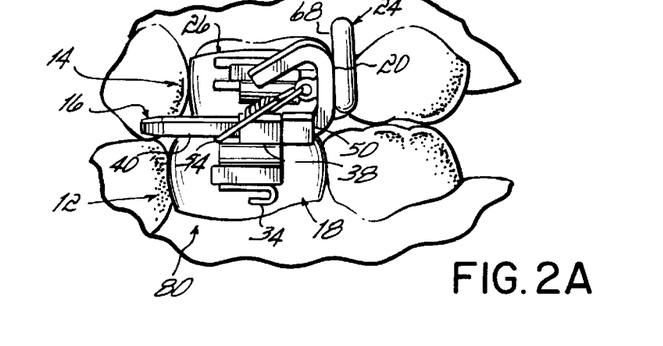
FIG. 2A is a partial view of the left side of the maxillary and mandibular jaws of a patient having a retrusive lower jaw, with the lower jaw in a corrected position and the maxillary and mandibular jaws in a closed relationship.

Referring to FIG. 2A, a portion of the left side of a patient's mouth is shown having another embodiment of the appliance positioned on the first and second molars on the left side of the mouth. This embodiment is essentially an inverted version of the embodiment of the appliance 10 shown in FIGS. 1 and 2 and like parts are identified with like numbers. As shown in FIG. 2A, in this inverted appliance 80, the first member 12 is mounted to the first molar on the mandibular jaw, while the second member 14 is mounted on the corresponding first molar of the maxillary jaw. In this embodiment, when the patient's mouth is in an uncorrected position, the obstruction surface 22 of the abutment/obstruction element 16 mounted on the mandibular tooth will contact the buccally extending projection 24 which is mounted on the maxillary tooth, thereby preventing bite closure. However, when the patient advances the lower jaw forward sufficient for the buccally extending projection 24 to clear the obstruction surface 22, then the patient may close the bite, with the buccally extending projection 24 biased against the now mesially positioned abutment surface 20 of the abutment/obstruction element 16 as shown in FIG. 2A.

Figure 4A:
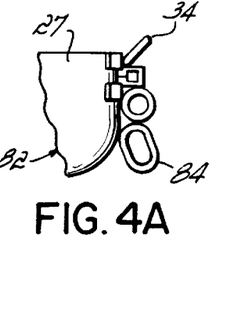
FIG. 4A is a partial mesial view of another embodiment of the mounting element.
Figure 5E:
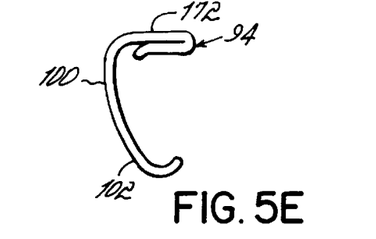
FIG. 5E is a side view of a further embodiment of the abutment/obstruction element.

Referring to FIG. 4A, another embodiment of the mounting element 82 is shown having a complementary mounting section 84 with an oval cross sectional shape. This oval complementary mounting section 84 is designed to receive a corresponding oval-shaped mounting section of an abutment/obstruction element such as the abutment/obstruction element shown in FIGS. 5A, 5B and 5E. The mounting sections shown in FIGS. 5A, 5B, and 5E are numbered 170, 87, and 172, respectively. The abutment/obstruction element 85 of FIG. 5A has an oval cross sectional shape throughout the length of the element, whereas the element 86 shown in FIG. 5B is formed from a wire having a round cross sectional shape. However, by extending the length of the mounting section 87 and doubling back with a portion of the wire, a substantially oval cross sectional shape may be created.

Figure 4B:
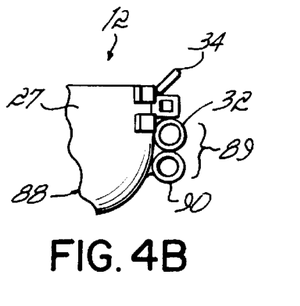
FIG. 4B is a partial mesial view of another embodiment of the mounting element.

Yet another embodiment of the mounting element 88 is shown in FIG. 4B. In this particular embodiment, the complementary mounting section 89 for slidingly engaging an abutment/obstruction element includes both the auxiliary tube 32 and a separate round tube 90 soldered occlusally relative to the auxiliary tube 32 shown in FIG. 4B. This complementary mounting section 89 is designed to receive the mounting section 91 of an abutment/obstruction element 92 such as the ones shown in FIGS. 5C and 5D. These particular abutment/obstruction elements 92, 93 are formed from round wire which is doubled over to form parallel wires. Preferably, the parallel wires are soldered together along the generally vertical portion forming the obstruction surface 20, from the gingival extremity 46 to the occlusal extremity 48. The mounting sections in FIGS. 5C and 5D are numbered 91 and 174, respectively.

Additional embodiments of the abutment/obstruction element 93, 94 of the appliance are shown in FIGS. 5D and 5E. When one of these particular embodiments is used, the abutment/obstruction element actually will have a slight camming action in cooperation with the buccally extending projection, and will assist a patient in moving the lower jaw forward as the patient closes the bite. Both the abutment and obstruction surfaces 96, 98, 100, 102 sweep gradually backward, and in fact, these abutment and obstruction surfaces 96, 98, 100, 102 actually overlap one another depending upon the position of the patient's jaws. When the element 93 of FIG. 5D is used, preferably the parallel wires are soldered together from the gingival extremity 46 of the abutment surface 96 to a point at least about two-thirds of the way along the length of the abutment/obstruction surfaces 96, 98.

Figure 7A:
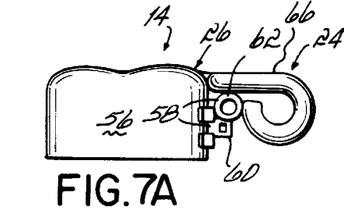
FIG. 7A is a mesial or front view of the embodiment of the second member shown in FIG. 3.
Figure 7B:
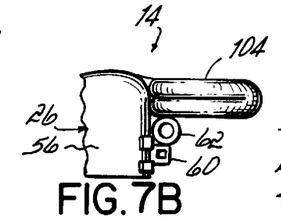
FIG. 7B is a partial mesial view of an alternate embodiment of the second member.
Figure 7C:
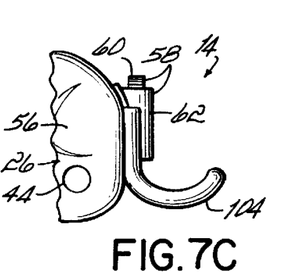
FIG. 7C is an occlusal or top view of the embodiment of FIG. 7B.
Figure 7D:
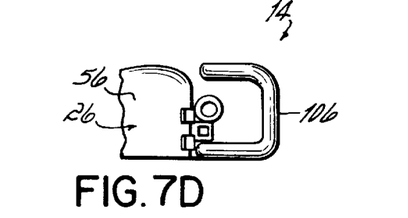
FIG. 7D is a partial mesial view of a further embodiment of the second member.
Figure 7E:
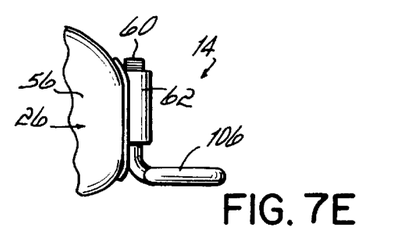
FIG. 7E is an occlusal or top view of the embodiment of FIG. 7D.

Additional embodiments of the buccally extending projection of the second member are shown in FIGS. 7B–7E. Referring to FIGS. 7B and 7C, in this particular embodiment, the buccally extending projection 104 is formed from a round wire, which is doubled over to form parallel round wires and curved to take on the shape of a hook which lies in a single plane substantially parallel to the occlusal plane. The portion of the projection 104 having the two exposed wire ends is soldered to the crown, while the opposite end, where the wire was bent to form two parallel wires, forms the most buccally extending portion of the projection 104. In addition, if desired, the parallel wires may be soldered to each other along the length of the projection 104. In this embodiment, the buccally extending projection 104 essentially cups or curves slightly around the abutment surface of the abutment/obstruction element when the jaws are closed. Referring to FIG. 7D and 7E, this embodiment of the buccally extending projection 106 has a U-shape, with the opening of the "U" oriented lingually. As seen in FIG. 7D, the buccally extending projection 106 is mounted gingivally relative to the combination tube. Alternatively, the buccally extending projection could have a vertically oriented mounting section mounted vertically onto the mesial buccal corner of the crown.

Figure 8:
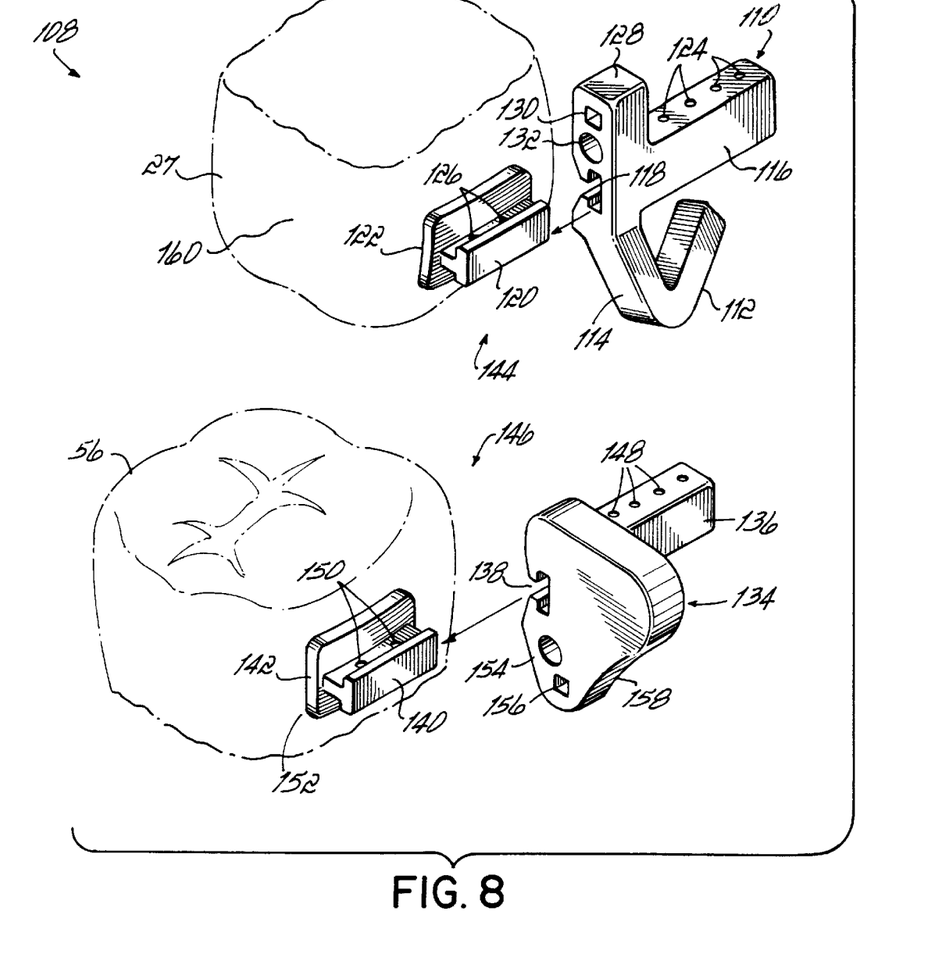
FIG. 8 is a perspective view of another embodiment of the first and second members.

Yet another embodiment of the appliance is shown in FIG. 8. This particular embodiment is a "track" version of the appliance 108. Referring to FIG. 8, the appliance 108 includes a first member 144 and a second member 146. The first member 144 includes an abutment/obstruction element 110 and a mounting element 160 for mounting the first member 144 to a tooth, with the abutment/obstruction element 110 including an obstruction surface 112, an abutment surface 114, and a mounting section 116. The second member 146 includes a buccally extending projection 134 and a mounting member 152 for mounting the second member 146.

In this particular embodiment, the mounting section 116 includes a track member 118. This track member 1 18 is slidingly engageable with the cooperative track member 120 on the complementary mounting section 122 which is mounted to the stainless steel crown 27. As seen in FIG. 8, the mounting section 116 includes several channels 124 formed in the occlusal-gingival direction, which may cooperate with similar occlusal-gingival channels 126 positioned in the complementary mounting section 122. With this particular embodiment, a doctor may slide the abutment/obstruction element 110 along the cooperative track member 120 until the desired positioning is reached. Once this desired positioning is reached, the doctor may insert ligatures, cotter pins or set screws into the channels 124, 126 or other similar apertures in order to temporarily fixate the abutment/obstruction element 110 in position. This feature gives the doctor added flexibility in moving the abutment/obstruction element 110 to different positions throughout the patient's treatment, much like the use of dog legs, collars, nicks or shims provide adjustment of the abutment/obstruction element 16 of the embodiment shown in FIGS. 1 and 2. In addition, the abutment/obstruction element 110 includes a post 128 having an archwire slot 130 and an auxiliary slot 132.

Referring to FIG. 8, the buccally extending projection 134 includes a mounting section 136 having a track member 138 which slidingly engages with the cooperative track member 140 on the complementary mounting section 142 which is mounted to a stainless steel crown 56. As with the first member 144 of this track embodiment, this second member 146 of the track version also includes a plurality of gingival-occlusal channels 148, 150 positioned in the mounting section 136 of the buccally extending projection 134 and in the complementary mounting section 142 of the mounting member 152. These channels 148, 150 allow the doctor to fix the buccally extending projection 134 in one of several positions using a ligature wire, cotter pin, set screw or the like. In addition, the buccally extending projection 134 includes an archwire slot 156 and an auxiliary slot 154 which extend from the abutment surface 158 of the projection 134 through to the other side of the projection 134.

The invention is not limited to the embodiments discussed in detail above, but on the contrary, is intended to cover various modifications and equivalent arrangements included within the spirit and scope of the appended claims.

What is claimed is:

1. An appliance for assisting a patient in maintaining a forward-moving force on the patient's mandibular jaw, comprising:

a first member including an abutment/obstruction element and a mounting element for mounting said first member to a tooth on one of the maxillary or mandibular jaws, said abutment/obstruction element having an abutment surface, an obstruction surface and a mounting section, said mounting section including a stem which is slidingly engageable with said mounting element; and a second member including a buccally extending projection and a mounting member for mounting said second member to a tooth on the other one of the maxillary or mandibular jaws, said second member being free of a permanent connection with said first member, said first and second members mountable so as to place said obstruction surface in generally vertical alignment with said buccally extending projection when the mandibular jaw is in its uncorrected position, causing said obstruction surface and buccally extending projection to strike each other when the patient attempts to close the mandibular and maxillary jaws with the mandibular jaw in its uncorrected position, thereby preventing complete closure of the mandibular and maxillary jaws unless the mandibular jaw is advanced in a forward direction from its uncorrected position sufficient to enable said buccally extending projection to clear said obstruction surface, at which point the patient may close the maxillary and mandibular jaws and bring said buccally extending projection into contact with said abutment surface so as to enable said buccally extending projection and said abutment surface to assist in maintaining a forward moving force on the patient's mandibular jaw.

2. The appliance of claim 1 wherein said first member is positionable on a maxillary tooth, said second member is positionable on a mandibular tooth, and said first and second members are mountable so as to prevent complete closure of the mandibular and maxillary jaws unless the mandibular jaw is advanced in a forward direction sufficient to locate said buccally extending projection mesial relative to said obstruction surface.

3. The appliance of claim 2 wherein said first and second members are adapted so as to be mounted to prevent complete closure of the mandibular and maxillary jaws unless the mandibular jaw is advanced in a forward direction sufficient to locate said buccally extending projection mesial relative to said obstruction surface and said abutment surface.

4. The appliance of claim 2 wherein said abutment surface extends in a generally gingival-occlusal direction between a gingival extremity and an occlusal extremity, and said obstruction surface extends generally distally from said abutment surface proximate said occlusal extremity.

5. The appliance of claim 4 wherein said generally gingivally-occlusally extending abutment surface is substantially vertical in the occlusal-gingival plane.

6. The appliance of claim 4 wherein said generally gingivally-occlusally extending abutment surface sweeps gradually backward in the distal direction from said gingival extremity to said occlusal extremity.

7. The appliance of claim 4 wherein said generally distally extending obstruction surface sweeps gingivally upward from said abutment surface proximate said occlusal extremity.

8. The appliance of claim 7 wherein said obstruction surface sweeps gingivally upward at an angle of from about 45° to about 65° relative to said abutment surface.

9. The appliance of claim 4 wherein said obstruction surface has a length of from about 0.29 inches to about 0.46 inches.

10. The appliance of claim 4 wherein said abutment surface has a length of from about 0.27 inches to about 0.40 inches.

11. The appliance of claim 1 wherein said first member is positionable on a mandibular tooth, said second member is positionable on a maxillary tooth, and said first and second members are mountable so as to prevent complete closure of the mandibular and maxillary jaws unless the mandibular jaw is advanced in a forward direction sufficient to locate said obstruction surface mesial relative to said buccally extending projection.

12. The appliance of claim 11 wherein said first and second members are mountable so as to prevent complete closure of the mandibular and maxillary jaws unless the mandibular jaw is advanced in a forward direction sufficient to locate said obstruction surface and said abutment surface mesial relative to said buccally extending projection.

13. The appliance of claim 11 wherein said abutment surface extends in a generally gingival-occlusal direction between a gingival extremity and an occlusal extremity, and said obstruction surface extends generally mesially from said abutment surface proximate said occlusal extremity.

14. The appliance of claim 13 wherein said generally gingivally-occlusally extending abutment surface is substantially vertical in the occlusal-gingival plane.

15. The appliance of claim 13 wherein said generally gingivally-occlusally extending abutment surface sweeps gradually forward in the mesial direction from said gingival extremity to said occlusal extremity.

16. The appliance of claim 13 wherein said generally mesially extending obstruction surface sweeps gingivally downward from said abutment surface proximate said occlusal extremity.

17. The appliance of claim 16 wherein said obstruction surface sweeps gingivally downward at an angle of from about 45° to about 65° relative to said abutment surface.

18. The appliance of claim 13 wherein said obstruction surface has a length of from about 0.29 inches to about 0.46 inches.

19. The appliance of claim 13 wherein said abutment surface has a length of from about 0.27 inches to about 0.40 inches.

20. The appliance of claim 1 wherein said mounting element for mounting said first member includes a mounting device selected from the group consisting of a crown, a buccal tube, a band, a bracket and combinations thereof.

21. The appliance of claim 1 wherein said mounting element includes a complementary mounting section for attaching said abutment/obstruction element to said mounting element.

22. The appliance of claim 21 wherein said mounting section stem and said complementary mounting section are slidingly engageable, whereby said abutment/obstruction element may be moved either mesially or distally relative to said mounting element, thereby moving said abutment surface and said obstruction surface either mesially or distally.

23. The appliance of claim 21 wherein said complementary mounting section includes a tube and said mounting section stem may be inserted into said tube.

24. The appliance of claim 23 wherein said mounting section includes a surface feature which contacts a rim of said tube when said mounting section stem has been inserted into said tube a particular distance, thereby preventing said mounting section stem from being inserted further into said tube.

25. The appliance of claim 23 wherein each of said complementary mounting section and said mounting section stem has a substantially rectangular cross-sectional shape.

26. The appliance of claim 21 wherein said mounting section stem includes a track member and said complementary mounting section includes a cooperative track member for engaging said track member, thereby enabling attachment of said abutment/obstruction element to said mounting element.

27. The appliance of claim 26 wherein said track member and said cooperative track member are slidingly engageable.

28. The appliance of claim 27 wherein said abutment/obstruction element includes a securing element for enabling said abutment/obstruction element to be secured to said mounting element.

29. The appliance of claim 28 wherein said securing element includes a channel passing through said mounting section, said complementary mounting section also having a channel, said mounting section channel and said complementary mounting section channel capable of being aligned so as to receive a fixation member therethrough.

30. The appliance of claim 29 wherein said fixation member is selected from the group consisting of a ligature wire, a cotter pin and a set screw.

31. The appliance of claim 29 wherein each of said mounting section and said complementary mounting section includes a plurality of channels, thereby enabling said abutment/obstruction element to be oriented in a plurality of positions relative to said mounting element, with at least one mounting section channel and at least one complementary mounting section channel being aligned in said plurality of positions so as to receive a fixation member therethrough.

32. The appliance of claim 26 wherein said abutment/obstruction element includes a slot selected from the group consisting of an archwire slot, an auxiliary slot and combinations thereof.

33. The appliance of claim 26 wherein said buccally extending projection includes a mounting section and said mounting member includes a complementary mounting section for attaching said buccally extending projection to said mounting member.

34. The appliance of claim 33 wherein said mounting section includes a track member and said complementary mounting section includes a cooperative track member for engaging said track member, thereby enabling attachment of said buccally extending projection to said mounting member.

35. The appliance of claim 34 wherein said track member and said cooperative track member are slidingly engageable.

36. The appliance of claim 35 wherein said buccally extending projection includes a securing element for enabling said buccally extending projection to be secured to said mounting member.

37. The appliance of claim 36 wherein said securing element includes a channel passing through said mounting section, said complementary mounting section also having a channel, said mounting section channel and said complementary mounting section channel capable of being aligned so as to receive a fixation member therethrough.

38. The appliance of claim 37 wherein said fixation member is selected from the group consisting of a ligature wire, a cotter pin and a set screw.

39. The appliance of claim 37 wherein each of said mounting section and said complementary mounting section includes a plurality of channels, thereby enabling said buccally extending projection to be oriented in a plurality of positions relative to said mounting element, with at least one mounting section channel and at least one complementary mounting section channel being aligned in said plurality of positions so as to receive a fixation member therethrough.

40. The appliance of claim 34 wherein said buccally extending projection includes a slot selected from the group consisting of an archwire slot, an auxiliary slot and combinations thereof.

41. The appliance of claim 1 wherein said abutment/obstruction element includes a securing element for enabling said abutment/obstruction element to be secured to said mounting element.

42. The appliance of claim 41 wherein said securing element includes a loop capable of receiving a ligature wire therethrough for fastening said abutment/obstruction element to said mounting element.

43. The appliance of claim 1 wherein said buccally extending projection includes a mounting section for attaching said buccally extending projection to said mounting member.

44. The appliance of claim 43 wherein said mounting section is fixedly attached to said mounting member.

45. The appliance of claim 1 wherein said buccally extending projection extends buccally from said mounting member for a distance of from about 7 mm to about 10 mm.

46. The appliance of claim 1 wherein said mounting member for mounting said second member includes a mounting device selected from the group consisting of a crown, a buccal tube, a band, a bracket and combinations thereof.

47. A method of assisting a patient to maintain a forward-moving force on the patient's mandibular jaw, comprising the steps of:
   mounting a first member on a tooth on one of the maxillary or mandibular jaws, said first member including an abutment/obstruction element having an abutment surface, an obstruction surface and a mounting section including a stem, said first member further including a mounting element for mounting said first member to a tooth on one of the maxillary or mandibular jaws, said stem being slidingly engageable with said mounting element; and
   mounting a second member on a tooth on the other one of the maxillary or mandibular jaws, said second member including a buccally extending projection and a mounting member for mounting said second member to a tooth on the other one of the maxillary or mandibular jaws, said second member being free of a permanent connection with said first member,
   said first and second members mounted so as to place said obstruction surface in generally vertical alignment with said buccally extending projection when the mandibular jaw is in its uncorrected position, causing said obstruction surface and buccally extending projection to strike each other when the patient attempts to close the mandibular and maxillary jaws with the mandibular jaw in its uncorrected position, thereby preventing complete closure of the mandibular and maxillary jaws unless the mandibular jaw is advanced in a forward direction from its uncorrected position sufficient to enable said buccally extending projection to clear said obstruction surface, at which point the patient may close the maxillary and mandibular jaws and bring said buccally extending projection into contact with said abutment surface so as to enable said buccally extending projection and said abutment surface to assist in maintaining a forward moving force on the patient's mandibular jaw.

48. The method of claim 47 wherein said method is performed to alleviate a condition selected from the group consisting of overbite, overjet, insufficient chin prominence, insufficient face length, jaw joint pain, jaw joint clicking, jaw joint stiffness, temporomandibular joint (TMJ) disorder, snoring, obstructive sleep apnea and combinations thereof.

49. A method of assisting a patient to maintain a forward moving force on the patient's jaw, comprising the steps of:
   mounting a first member on a tooth on one of the maxillary or mandibular jaws, said first member including an abutment/obstruction element having an abutment surface, an obstruction surface and a mounting section comprising a stem having a track member, said first member further including a mounting element for mounting said first member to a tooth on one of the maxillary or mandibular jaws, said mounting element including a complementary mounting section having a cooperative track member for engaging said track member; and mounting a second member on a tooth on the other one of the maxillary or mandibular jaws, said second member including a buccally extending projection having a mounting section including a track member, said second member further including a mounting member having a complementary mounting section including a cooperative track member for engaging said track member, said first and second members mounted so as to place said obstruction surface in generally vertical alignment with said buccally extending projection when the mandibular jaw is in its uncorrected position, causing said obstruction surface and buccally extending projection to strike each other when the patient attempts to close the mandibular and maxillary jaws with the mandibular jaw in its uncorrected position, thereby preventing complete closure of the mandibular and maxillary jaws unless the mandibular jaw is advanced in a forward direction from its uncorrected position sufficient to enable said buccally extending projection to clear said obstruction surface, at which point the patient may close the maxillary and mandibular jaws and bring said buccally extending projection into contact with said abutment surface so as to enable said buccally extending projection and said abutment surface to assist in maintaining a forward moving force on the patient's mandibular jaw.

50. The method of claim 49 wherein said method is performed to alleviate a condition selected from the group consisting of overbite, overjet, insufficient chin prominence, insufficient face length, jaw joint pain, jaw joint clicking, jaw joint stiffness, temporomandibular joint (TMJ) disorder, snoring, obstructive sleep apnea and combinations thereof.

* * * * *